United States Patent [19]

Napier et al.

[11] 3,992,432

[45] Nov. 16, 1976

[54] PHASE TRANSFER CATALYSIS OF HETEROGENEOUS REACTIONS BY QUATERNARY SALTS

[75] Inventors: Donald R. Napier, Corpus Christi, Tex.; Charles M. Starks, Ponca City, Okla.

[73] Assignee: Continental Oil Company, Ponca City, Okla.

[22] Filed: Feb. 18, 1975

[21] Appl. No.: 550,246

Related U.S. Application Data

[63] Continuation of Ser. No. 240,283, March 31, 1972, abandoned, which is a continuation-in-part of Ser. No. 778,324, Nov. 22, 1968, abandoned, which is a continuation-in-part of Ser. No. 628,534, April 5, 1967, abandoned.

[52] U.S. Cl. ............................. 260/465.1; 260/454; 260/513 H; 260/493; 260/598; 260/537 R; 260/604 HF; 260/632 C; 260/631 R; 260/649 R; 260/684; 260/687 R; 260/348.5 R; 260/652 R

[51] Int. Cl.$^2$ ........................................ C07C 120/04

[58] Field of Search ............... 260/454, 493, 537 R, 260/632, 649 R

[56] References Cited

UNITED STATES PATENTS

3,297,634    1/1967    Oxenrider et al. .................. 260/456

FOREIGN PATENTS OR APPLICATIONS

| 55,113 | 5/1968 | Poland |
| 55,535 | 5/1968 | Poland |
| 55,571 | 5/1968 | Poland |
| 876,125 | 8/1961 | United Kingdom |
| 912,104 | 12/1962 | United Kingdom |
| 975,368 | 11/1964 | United Kingdom |

OTHER PUBLICATIONS

Tet. Let., vol. 45, pp. 5489–5492 (1966).
Tet. Let., vol. 38, pp. 4621–4624 (1966).
Roczniki, Chemi Ann. Soc. Chim. Polonorum, vol. 40, pp. 1839–1847 (1966).
Roczniki, Chemi Ann. Soc. Chim. Polonorum, vol. 39, pp. 1223–1231 (1965).
Roczniki, Chemi Ann. Soc. Chim. Polonorum, vol. 40, pp. 1647–1656 (1966).
Roczniki, Chemi Ann. Soc. Chim. Polonorum, vol. 39, pp. 1401–1409 (1965).
Roczniki, Chemi Ann. Soc. Chim. Polonorum, vol. 39, pp. 1595–1602 (1965).
Roczniki, Chemi Ann. Soc. Chim. Polonorum, vol. 39, pp. 1799–1803 (1965).
Roczniki, Chemi Ann. Soc. Chim. Polonorum, vol. 39, pp. 1805–1810 (1965).
Roczniki, ChemiAnn. Soc. Chim. Polonorum, vol. 40, pp. 1647–1655 (1966).
Org. Chem. "Makozza", vol. 15, pp. 165–167 (1967).
Roczniki, Chemi Ann. Soc. Chim. Polonorum, vol. 41, pp. 1037–1046 (1967).

*Primary Examiner*—Lewis Gotts
*Assistant Examiner*—D. R. Phillips
*Attorney, Agent, or Firm*—Cortlan R. Schupbach, Jr.

[57] ABSTRACT

A process for catalyzing heterogeneous ionic organic reactions in a system of multiple liquid phases in which at least two of the reactants are each located in a different phase with respect to the other, the phases containing such reactants differing in polarity. Catalysis is effected by introducing to the system one of certain organic quaternary salts which are more soluble in the least polar reactant-containing phase than in the other reactant-containing phases. The quaternary salt catalysts utilized have the general structural formula $(AM)^+X^-$ where A is an organic portion of the salt molecule bonded to M by four covalent linkages, and preferably comprises a plurality of hydrocarbon radicals of either monovalent or polyvalent character, M is selected from the group consisting of nitrogen, phosphorus, arsenic, antimony and bismuth, and $X^-$ is an anion which will dissociate from the cation $(AM)^+$ in an aqueous environment, and is preferably selected from the group consisting of halogen and hydroxyl anions.

24 Claims, No Drawings

PHASE TRANSFER CATALYSIS OF HETEROGENEOUS REACTIONS BY QUATERNARY SALTS

This application is a continuation of our application Ser. No. 240,283, filed Mar. 31, 1972 now abandoned; which in turn was a continuation-in-part of our application Ser. No. 778,324, filed Nov. 22, 1968, now abandoned; which in turn was a continuation-in-part of our application Ser. No. 628,534, filed Apr. 5, 1967, now abandoned.

BACKGROUND OF THE INVENTION

1. Field of the Invention

This invention relates generally to a method of catalyzing heterogeneous ionic (polar) reactions in which the reactants are located in different liquid phases of differing polarity. More specifically, but not by way of limitation, the invention relates to a method for improving the reaction between a plurality of reactants in an environment in which one of the reactants is located predominantly in an aqueous liquid phase which is substantially immiscible with a contiguous organic liquid phase in which a second reactant is predominantly located so that significant reaction can only occur at the interface of the phases or by transfer of a functional group from one phase into another phase.

2. Description of the Prior Art

The organic quaternary salts of the Group VA elements of the Periodic Table of the Elements are known to be, in general, very stable, strong bases which are highly ionized in aqueous solutions to form a stable cation containing the pentavalent element bonded to its hydrocarbon substituents by strong covalent linkages. These quaternary salts have recently been found to be even more highly reactive in many ionic reactions than the corresponding sodium and potassium salts. It is also recognized that by adequately adjusting the configuration and length of the organic portions of the quaternary salt molecule, these compounds can be made to be readily soluble in organic solvents.

The possibility that the quaternary salts of the general type under discussion may be employed in a catalytic capacity in one reaction system has been explored and confirmed by Oxenrider et al. In their U.S. Pat. No. 3,297,634, these workers disclose the use of certain quaternary ammonium, phosphonium and arsonium salts for catalyzing the cyclization of a phosgene derivative of a bisphenate salt to produce a cyclic dicarbonate. The catalytic activity of the catalyst is postulated to arise from a mechanism in which the catalyst displaces the cationic portion of the phosgene derivative so as to render the derivative as a whole more soluble in a water-insoluble organic medium in which the desired cyclization transpires. The function of the quaternary salt is thus deemed to be that of solubilizing the reaction product of the phosgene-bisphenate reaction in an organic medium which provides the required environment for the occurrence of intramolecular cyclization. There does not appear to be involved in this catalysis any transfer across a phase interface of a functional group derived from a first reactant located in one liquid phase to a second reactant located in a second liquid phase with the quaternary salt acting as the acceptor of the functional group in the first phase and the donor of the functional group in the second phase.

BRIEF DESCRIPTION OF THE INVENTION

The present invention is based upon the discovery that certain organic quaternary salts of the elements of Group VA of the Periodic Table of the Elements (as in *Handbook of Chemistry and Physics*, Chemical Rubber Company, 45th Edition, (1964) p B2 can effectively catalyze heterogeneous reactions in which the reactants are located in distinct liquid phases by transferring ions or other reactive or functional groups across the phase interface. The underlying phase transfer mechanism which appears to account for the catalytic activity of the quaternary salts appears to have general applicability to heterogeneous ionic organic reactions in which two or more reactants which are capable of reacting with each other to some degree by a shift of a functional or reactive ion or group between the reactants are disposed in two or more distinct phases. In practically every instance, the distinct phases which contain the reactants will differ in polarity and the quaternary salt will be selected to be preferentially soluble in the less polar of the two phases. In the great majority of cases, though not in all, one of the reactants will be located in an aqueous phase and the other in an organic phase, and the quaternary salt will be substantially more soluble in the organic phase than in the aqueous phase.

The quaternary salts used in the present invention include one or more groups having the formula $(AM)^+X^-$ where M is a pentavalent ion derived from an element of Group VA of the Periodic Table, and A is an organic portion of the salt molecule bonded to M by four covalent linkages. $X^-$ is an anion which will dissociate from the cation $(AM)^+$ in an aqueous environment. As indicated, the group $(AM)^+X^-$ may be repeated; as in the case of dibasic quaternary salts having two pentavalent Group VA ions substituted in the manner described. The salt may also be polymeric in character, with the described group repeated a number of times.

The preferred quaternary salts for use in the invention have the formula $(R_1R_2R_3R_4M)^+X^-$ where M and $X^-$ are as hereinbefore defined, and $R_1$, $R_2$, $R_3$, and $R_4$ are monovalent hydrocarbon radicals preferably selected from the group consisting of alkyl, alkenyl, aryl, alkaryl, aralkyl, and cycloalkyl radicals. The total number of carbon atoms in $R_1$, $R_2$, $R_3$, and $R_4$ should be at least 18 and is preferably from about 28 to 40. No theoretical maximum number of carbon atoms for inclusion in the quaternary salts exists, although in general, where the phases involved in the reaction system are aqueous and organic, about 70 carbon atoms represents the upper limit imposed by certain practical limitations.

In addition to the definitive specific structural characteristics of the quaternary salts which are set out in the preceding paragraph, it is also essential to the successful practice of the invention that the salt utilized by selected to have substantial greater solubility in the less polar of the two reactant-containing phases than in the more polar of the two phases. Since, in the majority of instances of practice of the invention, the liquid phases involved will be aqueous and organic or oleaginous, the carbon atom content and structural configuration of the quaternary salt will usually be selected to impart to the salt a marked solubility in the organic phase.

In the actual practice of the process of the invention for effecting phase transfer catalysis of heterogeneous ionic organic reactions, the reactants are located in their respective phases and the quaternary salt catalyst is added to the system. The system is then generally stirred, and heat may be applied if the reaction is endothermic in nature. The catalysis can generally be effected at atmospheric pressure, but pressure considerations are not critical to the practice of the invention except as the requirements of a particular system and type of reaction may dictate. Stated differently, the catalytic effect of the quaternary salts can be experienced at a variety of temperatures and pressures for reactions of different types carried out in various multiphase systems, it being only necessary that for a given system and reaction, some type of ionic chemical reactivity will occur in a finite degree at some temperature and pressure in the absence of the catalyst. Thus, given a multiphase system containing reactants possessing theoretical ionic reactivity disposed in the several phases, the necessary and optimum temperature and pressure for catalyzing such reaction can be determined empirically.

It should be further pointed out that the terms catalytic activity and catalysis as they are here used are intended to mean that a finite increase in the extent to which, or the rate at which, the reactants in the several phases react with each other is caused to occur by the presence in the system of the quaternary salt. Thus, there may or may not be an economic advantage to conducting the catalysis in the case of a particular reaction, but, as will be hereinafter shown, in many different generic types of heterogeneous ionic reactions, a striking improvement in reactivity is realized which makes the heterogeneous or multiphase environment a much more attractive route by which to produce certain reaction products than any method heretofore available.

From the foregoing description of the invention, it will have become apparent that it is a major object of the invention to catalyze ionic organic reactions between reactants disposed in different phases of a system containing multiple liquid phases.

Another object of the invention is to provide a catalyst capable of accepting an anion from a reactant which is substantially entirely disposed in a liquid phase and transferring such anion into a second liquid phase which is substantially immiscible in the first phase, and there yielding up the anion to a second reactant which is substantially entirely disposed in such second liquid phase.

A more specific object of the invention is to provide a method for catalyzing heterogeneous displacement reactions in which an anion from one reactant displaces an anion from a second reactant, such reactants being located in different liquid phases.

Another relatively specific object of the invention is to provide a new process for preparing dichlorocarbene derivatives.

Another object of the invention is to improve the ease with which esters may be hydrolyzed by contact with alkali metal hydroxide.

An additional object of the invention is to enhance the ease with which various organic compounds can be oxidized by reaction with inorganic oxidizing agents.

A further object of the invention is to provide a new method for converting carbonyl compounds to alcohols.

Another object of the invention is to usefully employ a newly discovered property of certain quaternary salts in the capacity of a catalyst for promoting ionic organic heterogeneous reactions.

Still another object of the invention is to enhance the oxidation of olefins with oxidizing agents in the presence of certain metal or metal oxide catalysts.

In addition to the foregoing described objects and advantages, additional objects and advantages of the invention will become apparent as the following detailed description of the invention is considered.

DESCRIPTION OF THE PREFERRED EMBODIMENTS

Before discussing more specific aspects of the present invention, a brief review of the chronology of the conception and evolution of the invention will be an aid to its understanding. In the laboratory, alkyl cyanides have usually been prepared by carrying out a displacement reaction of the type:

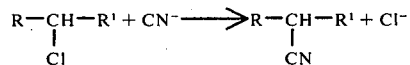

wherein R and $R^1$ are the same or different hydrocarbon materials and generally are alkyl groups in a special and expensive solvent such as dimethylsulfoxide. In an attempt to find a less difficult and expensive route to the production of alkyl cyanides, an effort was made to bring about the displacement reaction by placing an inorganic cyanide compound in an aqueous solution and an organic halide in an organic solvent and mixing the two in the presence of an organic quaternary ammonium salt. The reaction proceeded quite well. In subsequent studies of the reaction mechanism involved, it was determined by the use of radioactive tracer atoms that the quaternary salt actually acts as a transporting instrumentality which receives cyanide anions from the inorganic cyanide and transfers these either from or across the phase interface into the organic phase. There the anions are yielded up to the alkyl halide and the displaced halide ion is received by the quaternary salt and transferred back to the aqueous phase. The mechanism can be approximated schematically as follows:

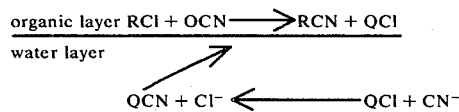

where Q represents the cationic portion of quaternary salt and R has the meaning heretofore given. It was not clearly established whether the cyanide anions are picked up by the cation from the quaternary salt at the phase interface or deep within the water layer, or both. Nevertheless, the possible general applicability of this phase transfer mechanism occurred to us, and has subsequently been confirmed with respect to heterogeneous ionic organic reactions in which an anion is transferred across a liquid phase interface and enters into a reaction with a reactant different from that from which it originated, said reactant being located substantially entirely in the phase into which the anion is transferred.

The phase transfer catalytic activity is characteristic of the quaternary salts of the Group VA elements having the general formula $(AM)^+X^-$ where M is a pentavalent ion of an element selected from the group consisting of nitrogen, phosphorus, arsenic, antimony and bismuth; A is an organic group bonded to the Group VA element by four covalent bonds, and $X^-$ is an anion which will dissociate from the cation $(AM)^+$ in an aqueous environment. Mixtures of such salts may likewise be utilized in the practice of the invention. It should be further pointed out that double or multifunctional quaternary salts in which the general formula $(AM)^+X^-$ is repeated a plurality of times can also be utilized effectively An example of this type of compound is N,N,N',N'-tetramethyl-N; N'-dioctadecyl-x-dodecyl-y-xylene-$\alpha,\alpha'$-diammonium dichloride which has the formula

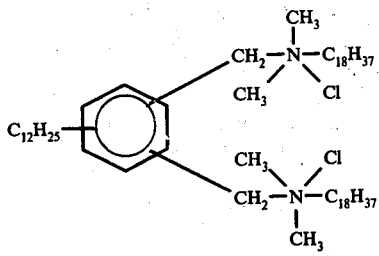

The quaternary salts of Group VA elements preferably have the formula $(R_1R_2R_3R_4M)^+X^-$ where M is as hereinbefore defined, and $R_1$, $R_2$, $R_3$ and $R_4$ are monovalent hydrocarbon radicals, and $X^-$ is as hereinbefore defined. Still more preferably, $R_1$, $R_2$, $R_3$ and $R_4$ are selected from the group consisting of alkyl, alkenyl, aryl, alkaryl, aralkyl, and cycloalkyl radicals, and $X^-$ is selected from the group consisting of halide ions and hydroxyl ions. From the latter group, the halide quaternary salts appear to function best in the catalysis, and of these the chloride and bromide salts are most preferred. Of the several Group VA elements which may be present in the quaternary salt, nitrogen and phosphorus are generally preferred.

The number of carbon atoms in the hydrocarbon substituents $R_1$, $R_2$, $R_3$ and $R_4$ of the Group VA metal may vary considerably so as to contain from 1 to about 25 or more carbon atoms in each instance. The total carbon atom content, however, of all these groups is preferably at least 18 carbon atoms per atom of Group VA metal, and there is no theoretical upper limit on the number of carbon atoms, although about 70 carbon atoms constitutes a practical upper limit imposed by economic factors. It is also highly preferable that each of the hydrocarbon substituents $R_1$, $R_2$, $R_3$ and $R_4$ contain more than a single carbon atom. Examples of suitable quaternary salts are hexadecyltrihexylammonium bromide; trioctylethylammonium bromide; tridecylmethylammonium chloride; didodecyldimethylammonium chloride; tetraheptylammonium iodide; dioctadecyldimethyl ammonium chloride; tridecylbenzylammonium chloride; ditricosylmethylammonium chloride; tributyldecylphosphonium iodide; triphenyldecylphosphonium iodide, tributylhexadecylphosphonium iodide; tricaprylyldodecylammonium p-toluene sulfonate; tribenzyldecylarsonium chloride; tetranonylammonium hydroxide; tritridecylphenylstibonium chloride; triahentriacontylmethylbismuth chloride; N,N,N',N'-tetramethyl-N,N'-ditetradecyl-p-xylene-$\alpha,\alpha'$- diammonia dichloride; 1-methyl-1-(N-octadecanoyl-2-aminoethyl)2-heptadecyl-4,5-dihydro-1,3-diazole methylsulfate; N,N,N',N'-tetramethyl-N,N'-dioctadecyl-x-dodecyl-y-xylene$\alpha,\alpha'$-diammonium dichloride; N,N-dioctadecyl-N-methyl-N-(sodiocarboxylmthyl)-ammonium chloride; N,N,N',N'-tetramethyl-N,N'-dioctadecyl-p-xylene-$\alpha,\alpha'$-diammonium dichloride; N,N,N',N'-tetramethyl-N,N'dioctadecyl-1,2-ethyldiammonium dibromide; N,N'-dimethyl-N,N,N',N'-tetraheptadecyl-2-butene-1,4-diammonium chloride.

In the phase transfer mechanism which accounts for the catalytic activity of the quaternary salt, the rate at which the reaction between the diverse phase reactants proceeds as a result of this transfer mechanism can be said to be at a maximum when the equality $k_nf_n = k_pf_p$ exists. Here, $k_n$ refers to the reaction rate constant of the quaternary salt (in yielding up the transferred anion) in the less polar of the reactant-containing phases, and $k_p$ refers to the reaction rate constant of the quaternary salt (in accepting the transferred anion) in the more polar of the reactant-containing phases. $f_n$ refers to the mole fraction of the quaternary salt which distributes itself in the less polar reactant-containing phase at equilibrium and $f_p$ refers to the mole fraction of the quaternary salt present in the most polar reactant-containing phase. Now since the reactivity of the quaternary salt in the more polar phase (as expressed by the rate constant $k_p$) is always larger and is generally very great as compared to its reactivity in the less polar phase ($k_n$), the desired equality will be more nearly approached if $f_n$ is larger than $f_p$, that is, if more of the quaternary salt is distributed in the less polar phase than in the more polar phase. From these considerations, it follows that the quaternary salt should be selected to be more soluble in the least polar of the reactant-containing phases than in the other reactant-containing phases. This preferential solubility is also desirable because the quaternary salts generally exhibit better thermal stability in the phase of lesser polarity.

The point of the discussion relative to preferential solubility of the quaternary salt in the least polar of the reactant phases is that the particular chain length and configuration of the organic portion of the cationic portion of the quaternary salt will be, in large part, dictated by this consideration. They will also be in part determined by the necessity for the quaternary salt to remain stable at the temperature at which the particular heterogeneous reaction is to be carried out, and, of course, the quaternary salt must be essentially inert or non-reactive with respect to all materials in the reaction mixture except the reactants themselves. In most instances, this will mean that the quaternary salt will demonstrate no appreciable reactivity with the immiscible solvents utilized to contain the several reactants.

The amount of the quaternary salt which is added to the heterogeneous system to effect catalysis is subject to considerable variation. As a general proposition, reaction rates will be increased by raising the temperature, or by raising the concentration of the quaternary salt in the system, or both. No theoretical maximum or upper limit upon the amount of quaternary salt utilized probably exists, but practical considerations, such as the need to separate the catalyst from product compounds, require that as little of the salt be used as is necessary to achieve a satisfactory rate of reaction. In general, however, the amount of the quaternary salt utilized will be from about 0.01 weight percent to about 50 weight percent, based on the weight of the reactant in the least polar phase. An amount of from about 1 to about 20 weight percent is preferred.

As has hereinbefore been indicated, the phase transfer mechanism of catalysis which underlies the present invention appears to have general applicability to heterogeneous ionic reactions in which two or more reactants capable of reacting with each other to some degree by a transfer of an ion or functional group are disposed in two or more distinct phases. Thus, a marked catalytic effect has been observed in heterogeneous reactions of the displacement type, in the preparation of dichlorocarbene compounds, in the oxidation of various organic compounds with inorganic oxidizing agents, in the conversion of carbonyl compounds to alcohols, in the saponification of esters, in the hydrolysis of sulfonyl chlorides, and in the oxidation of olefins. Examples of the practice of the present invention to carry out reactions of these general types will contribute to a fuller understanding of the invention. Examples 1–8 exemplify the use of quaternary salts for catalyzing displacement reactions.

Subsequent to filing our earlier applications, we have done considerable work on oxidation of olefins to various end products in the presence of certain known catalyst and certain known oxidizing agents. It is pointed out that the quaternary salt does not change the product, but rather enhances the reaction.

For example, it is known that olefinic compounds can be oxidized to produce various oxidation products with hydrogen peroxide, periodic acid, potassium permanganate and the like. It is also known that metal compounds will catalyze the reaction. (See L. F. Fieser "Reagents for Organic Synthesis" pages 457–478; R. Poppo et al., *J. Organic Chemistry*, 21, 478–479 (1956); U.S. Pat. No. 3,057,915, Riemenschneider et al.: R. Poppo et al., *Bal. Res. Council of Israel*, 5A 300–301 (1956). Thus, it is known when one oxidizes an olefin with periodic acid in presence of osmium the product is primarily an aldehyde, whereas, when ruthenium is the catalyst, the product is primarily the carboxylic acid. It is also known that aqueous hydrogen peroxide is rapidly decomposed by catalytic metal compounds thereby destroying the ability of the peroxide to catalyze the oxidation reaction. Thus, in an aqueous medium, the addition of a metallic catalyst is self-defeating. For example, osmium tetraoxide catalyzes the oxidation of cyclohexene by hydrogen peroxide to yield cis-1,2-diols. An important requirement in this system is that the hydrogen peroxide be anhydrous, a condition normally met by using t-butyl alcohol as a solvent. If much water is present, the hydrogen peroxide is rapidly decomposed to give oxygen and water and consequently little or no oxidation of the olefin. (Miles et al., *J. Am. Chem. Soc.*, 58, 1302 (1936). The quaternary compounds of this invention serve not only as phase transfer agents with aqueous $H_2O_2$ but also stabilize the $H_2O_2$ against decomposition.

In carrying out the process of the invention, it is only necessary that the reactants, e.g., olefin and oxidation agent solution be in the liquid state. We prefer to carry out the reaction in a hydrocarbon solvent since such solvents facilitate the product removal. The pressure can vary over a wide range as well as can the temperature. Normally, ambient temperature will be utilized and sufficient pressure to maintain the olefin in the liquid state. In most cases, atmospheric pressure is utilized except with such low boiling olefins such as ethylene, propylene and the like. Thus the normal temperature range will be 30° to 100° C and only sufficient pressure utilized to maintain the system in the liquid state. The reaction can be carried out at subambient temperatures or even under vacuum; however, as with most reactions, temperature and pressure enhance the reaction so no advantage is gained by lowering temperature or pressure. The reaction proceeds normally at ambient conditions; and thus, economically, one would not normally choose to use high temperatures and pressures. The reaction is exothermic; therefore, the temperature will be in excess of room temperature after the reaction is initiated. If one so desired, he could utilize much higher temperatures and pressures; but again, this is not necessary, however, it is pointed out that temperatures and pressures can be varied widely if desired. The paraperiodic acid, $H_2O_2$ and potassium permanganate are utilized in aqueous solution having at least 5 percent water and an excess of the solution is desirable to insure complete oxidation especially when using $OsO_4$. This is not required, however, when $RuO_4$ is the catalyst. The various metal catalysts will be used with or without water as in the prior art.

The olefins which can be oxidized by the method of this reaction include those compounds having one or more olefinic unsaturations and can be aliphatic, cycloaliphatic, or aryl olefins. The aromatic-olefins and cyclo-olefins can have alkyl substituents, and the aliphatic olefins can be normal or branched. These olefinic compounds can vary in molecular size over a wide range so long as they are liquid at reaction conditions. It should be obvious that the molecular size would not affect the oxidation. For example, the aliphatic olefins can contain 2 to 50 carbon atoms or more. Most generally, the olefins of interest will contain 4 to 30 carbon atoms. The cyclo-olefins generally contain 4 to 34 carbon atoms, preferably 4 to 8 carbon atoms. The aryl olefins can be mono or poly nuclear but most generally will contain one to two rings. Here again, the carbon atom range can be up to 50 carbon atoms or more, the lower limit being obviously 8, e.g., styrene, and most generally they will be styrene or alkyl substituted styrene of 8 to 18 carbon atoms.

Examples of such olefins include ethylene; pentene-2; octadiene-1,5; dodecene-4; pentacosene-6; nonacosene-3; hexatriacontene-1; pentacontene-15; 3-methylhexene-1; 4-ethyloctene-2; 2-ethyl-5-butyl-23-hexyl-33-propylpentatriacontene-3; cyclobutene; cyclohexene; cyclododecene; cyclotriacontene; 1-ethyl-4-propyl-cyclooctene; 1-ethyl-3-butyl-5-pentylcyclododecene; styrene; 3-methylstyrene; stilbene; tetraphenylethylene; vinylnaphthalene; vinylanthracene; 4-butyl-1-vinylnaphthalene; 2,7-diphenyldodecene-3; 1-hexene; 1-octene; 1-decene; 1-dodecene; 1-tetradecene; internal isomers of decene; dodecene; tetradecene; hexadecene; octadecene; eicosene; vinylcyclohexene; 1,3-butadiene or alkyl substituted butadiene; vinyl chloride; vinyl acetate; oleic acid; linoleic acid; and the like, such compounds being well known to the art.

The catalysts which are useful in this invention are the oxides of the metals previously disclosed. The osmium and ruthenium tetraoxides are preferred for oxidation of olefins; however, osmium or ruthenium can be added as the pure metal in finely divided state, the lower oxides or as a salt such as the halides, preferably chlorides, sulfates, acetates, adipates, nitrates, citrates, hydroxides and the like. The oxidizing agent will oxidize the metal to the active oxide. Obviously, it is preferable to add the metal as the oxide since any oxidizing agent utilized for oxidizing the catalyst is not available for oxidizing the olefin. As is true with most catalysts, only small quantities are employed, usually 0.05 percent to 2 percent; however, smaller amounts can sometimes be employed and larger amounts, while not needed, are not objectionable.

A generalized displacement reaction can be represented by the equation $$RX + A^- \xrightarrow{Q} RA + X^-$$

where RX is, for example, an alkyl halide, $A^-$ is an anion, and Q is the quaternary salt.

In attempting to react sodium cyanide with 1-chlorohexadecane according to the reaction $$NaCN + C_{16}H_{33}Cl \rightarrow C_{16}H_{33}CN + NaCl$$

no perceptible reaction will occur unless a solvent is used which will dissolve both the reactants. Such solvents as dimethyl sulfoxide and N,N-dimethylformamide are useful for this purpose, but are expensive and require processes which enable the solvent to be recovered in high purity.

This reaction was carried out by the process of the present invention as follows:

EXAMPLE 1

A reaction mixture was prepared from 500 grams of potassium cyanide, 400 ml of water, 5 ml of methanol containing about 0.1 mg of $C^{14}$ labeled sodium cyanide, 500 ml (426 grams) of 1-chlorohexadecane, 41.8 grams of N,N-ditallow-N,N-dimethylammonium chloride solution (25% isopropanol) and 50 ml of dodecane. The reaction mixture was heated under reflux (108° C) for 8 hours. The progress of the reaction was followed by assaying the reaction mixture for radioactive cyanide. At the end of the heating time, the reactivity level indicated that 91% of the 1-chlorohexadecane had been converted to hexadecyl cyanide. Analysis of the reaction product by gas liquid partition chromatography indicated that 87% of the reaction mixture had been converted to hexadecyl cyanide.

The run was then repeated in every detail except that no N,N-ditallow-N,N-dimethylammonium chloride was added, and a reaction time of 48 hours was allowed, rather than 8 hours. At the end of the 48-hour period, less than 1% of the 1-chlorohexadecane had undergone reaction.

EXAMPLE 2

A mixture of 120 grams of 1-chlorodecane, 100 ml of water, 100 grams of potassium cyanide, and 8 ml of methanol solution containing about 0.1 mg $C^{14}$ labeled sodium cyanide was heated under reflux (102°–3° C) for 5 hours. During this time, samples were periodically withdrawn from the reaction mixture and assayed for radioactivity. After this time, 5.0 ml of a 50% isopropanol solution of dodecylbenzyltrimethylammonium chloride was added to the reaction mixture, and refluxing was continued. The data in Table I show that no reaction took place until the quaternary ammonium salt was added:

TABLE I

| Time | $C^{14}$ Radioactivity Assay of Organic Layer (Counts) | % Reaction of 1-Chlorodecane |
|---|---|---|
| 8:48 AM | 262 | 0 |
| 9:48 AM | 114 | 0 |
| 10:55 AM | 90 | 0 |
| 12:21 PM | 79 | 0 |
| 1:28 PM | 125 | 0 |
| Quaternary Salt added at 1:28 PM | | |
| 1:36 PM | 2751 | 0.33 |
| 2:01 PM | 4396 | 1.44 |
| 2:50 PM | 8380 | 3.41 |
| 4:06 PM | 13189 | 6.90 |
| 4:51 PM | 15673 | 8.70 |
| 7:12 PM | 24011 | 15.16 |
| Next morning: | | |
| 8:15 AM | 65247 | 44.68 |

EXAMPLE 3

A reaction mixture was prepared from 419 grams of sodium iodide, 200 ml of water, 200 grams of 1-chlorohexadecane, and 20 grams of ditallowdimethylammonium chloride solution (25% in isopropanol). The reaction mixture was heated at 108° C for 5 hours and at 125° for 8 hours. After this time, 99% of the 1-chlorohexadecane had been converted to 1-iodohexadecane.

EXAMPLE 4

A reaction mixture containing 50 grams of 1-bromodecane (0.226 mole), 100 grams of sodium chloride (1.71 mole), 100 ml water, 12.5 ml of 1-decene (used as an internal gas liquid partition chromatography standard) and 1 gram of tricaprylylmethylammonium chloride was heated at 103° C over a period of 6 hours, during which time analytical samples were periodically removed from the reaction mixture. Equilibrium was essentially reached in the reaction mixture after 4 hours (at equilibrium, 13.86% of 1-bromodecane and 86.14% of 1-chlorodecane were present, corresponding to a mole ratio RCl/RBr = 9.08). This corresponded to an equilibrium constant $$K = \frac{(RCl)(Br)}{(RBr)(Cl)} = 1.18$$

EXAMPLE 5

A reaction mixture containing 50 grams of 1-bromodecane (0.226 mole), 250 grams of sodium iodide (1.67 moles), 50 ml water, 13 ml 1-decene and 0.5 gram tricaprylylmethylammonium chloride was heated to 107°–108° C for 2 hours with stirring. The progress of the reaction was followed by periodic removal of gas liquid partition chromatography samples. Nearly quantitative (95.4%) conversion of the bromide to iodide was obtained during the first hour, rising to 99.3% conversion during the second hour.

EXAMPLE 6

A reaction mixture containing 55 grams of 1-bromodecane (0.25 mole), 270 grams of sodium acetate trihydrate (1.98 moles) 12.5 ml of 1-decene and 10 grams of tricaprylylmethylammonium chloride was heated to 105° C for 2 hours with mechanical stirring. The progress of the reaction was followed by periodic sampling and gas liquid partition chromatography analysis of the organic layer. The reaction forming decyl acetate was essentially complete after 1 hour. A plot of the data showed reasonably good first-order kinetics.

EXAMPLE 7

A mixture of 100 grams (0.45 mole) of 1-bromodecane, 160 grams (1.98 moles) of sodium thiocyanate, 50 ml water and 10 grams of tricaprylylmethylammonium chloride was heated to 88°–105° C with stirring over a period of 2 hours. Examination of the reaction mixture by gas liquid partition chromatography showed that 100% conversion of the 1-bromodecane had occurred to give 1-thiocyanodecane.

EXAMPLE 8

A mixture of 100 grams (0.45 mole) of 1-bromodecane, 105 grams (1.3 moles) of potassium cyanate, 25 ml of water and 10 grams of tricaprylylmethylammonium chloride was heated with stirring. After 15 minutes the temperature had reached 85° C where gas evolution started. Heating at this temperature was continued for 15 minutes, then 125 ml of water was added and the mixture was heated under reflux for 0.5 hours. On cooling, a solid crystallized. The solid product was collected, washed with petroleum ether and dried (20 grams). This product was analyzed by nuclear magnetic resonance to be N,N′-didecylurea. The organic layer remaining after removal of the urea (65 grams) was 1-bromodecane plus a small amount of 1-chlorodecane as determined by gas liquid partition chromatography.

Examples 9 and 10 exemplify the use of phase transfer catalysis employing a quaternary salt for hydrolyzing esters by the phase transfer of a hydroxyl ion from an aqueous phase to a reactant in an immiscible organic phase. The reaction may be generally expressed

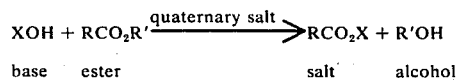

$$\text{XOH} + \text{RCO}_2\text{R}' \xrightarrow{\text{quaternary salt}} \text{RCO}_2\text{X} + \text{R}'\text{OH}$$

base    ester    salt    alcohol

Generally, ester saponifications of this type require a common solvent for base and ester and long reaction times at about 100° C. Using the present invention, the reaction proceeds under mild conditions of temperature (from about 30°–50° C) and becomes exothermic in progress.

EXAMPLE 9

A mixture of 50 grams (0.29 mole) of dimethyl adipate, 25 ml (35 grams) of 50 weight percent aqueous sodium hydroxide solution (0.43 mole of NaCd), 50 ml n-decane, and 5 grams of tricaprylylmethylammonium chloride was stirred at room temperature. The temperature immediately began to rise and reached 80° C after about 5 minutes, at which time and temperature methanol distilled from the reaction mixture. (No external heating was used.) The mixture was then stirred for an additional hour. After cooling, the aqueous layer was separated from the reaction mixture and diluted with 100 ml water. Acidification with concentrated hydrochloric acid gave solid adipic acid which was collected and dried (34 grams—108% conversion based on NaOH). The organic layer was not worked up.

EXAMPLE 10

A mixture of 100 grams (0.35 mole) of n-hexadecyl acetate, 50 grams of 50% aqueous sodium hydroxide solution (25 grams — 0.62 mole of NaOH) and 1 gram of tricaprylylmethylammonium chloride were stirred in a beaker. After 10 minutes, 50 ml of water was added to the reaction mixture, and the temperature rose to 54° C. After stirring for 2 hours, the organic layer solidified. The mixture was then heated to 50° C for 20 minutes. After cooling, the solid which separated was collected on the filter, washed with water and dried to give 41 grams (95%) of 1-hexadecanol having a melting point of 43°–48° C.

Examples 11–13 demonstrate the preparation of dichlorocarbene derivatives by reacting chloroform with an olefin and base in a heterogeneous system in the presence of a quaternary salt catalyst according to the generalized reaction

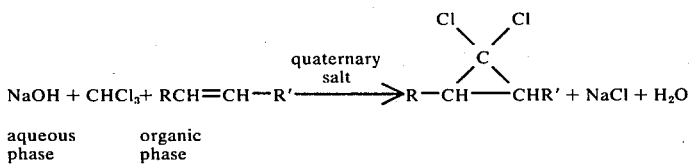

$$\text{NaOH} + \text{CHCl}_3 + \text{RCH}=\text{CH}-\text{R}' \xrightarrow{\text{quaternary salt}} \text{R}-\overset{\displaystyle \overset{\text{Cl}}{\underset{\text{Cl}}{\diagdown\!\diagup}}\!\!\!\text{C}}{\text{CH}}-\text{CHR}' + \text{NaCl} + \text{H}_2\text{O}$$

aqueous    organic
phase      phase

This reaction is not conventionally run where water is present in the system because of extremely rapid hydrolysis of chloroform to carbon monoxide. Other workers have used such expensive bases as sodium alkoxides, potassium t-butoxide, or lithium alkyls, always in completely anhydrous systems, rather than the aqueous alkali metal hydroxide solution.

EXAMPLE 11

25 ml (37.5 grams, 0.31 mole) of chloroform was added dropwise to a mixture of 100 ml (75 grams, 0.67 mole) of 1-octene, 100 ml (140 grams) of 50% aqueous sodium hydroxide solution (70 grams, 1.75 moles NaOH) and 5.0 grams of tricaprylylmethylammonium chloride. The chloroform addition rate was controlled such that the temperature was 45°–50° C (addition over a period of about 0.5 hour). After the addition was complete, the reaction mixture was stirred at room temperature for a period of one hour. The organic layer was then separated and washed with two 200 ml portions of water (last wash with water gave an emulsion which was broken with 10 ml saturated NaCl solution). At this point, the organic product layer was analyzed by gas liquid partition chromatography and found to contain 59.4% of 1-octene, 9.56% chloroform, 2.2% of a first unknown A, and 28.9% of a second unknown B.

The product was distilled through a 12-inch vacuum-jacketed Vigreaux column to give a fraction which had a boiling point of 49° C at 0.2–0.5 mm Hg, and which weighed 28 grams and contained chlorinated products (plus about 1% of 1-octene). The trap material consisting of 11 grams contained 31% of the products as analyzed by gas liquid partition chromatography. The two unknowns in the product were separated by preparative gas chromatography. The major product, the second unknown B, was identified as the expected 2-hexyl-1,1-dichlorocyclopropane by nuclear magnetic resonance, mass spectra and chlorine analysis. The minor product, unknown A, was not identified with certainty, but was thought to be either 3-(trichloromethyl)-1-octene or 2-pentyl-3-methyl-1,1-dichlorocyclopropane. The isolated selectivity (based on chloroform) of the dichlorocyclopropane was 65%, while that of the minor product A was 5.2%.

EXAMPLE 12

Aqueous 50% sodium hydroxide solution (25 grams or 0.63 mole NaOH) was added dropwise to a mixture of 100 grams (1.19 mole) of 1-hexene, 50 grams (0.42 mole) of chloroform and 5.0 grams tricaprylylmethylammonium chloride. The addition was controlled such that the temperature was maintained at 40° C. (The addition was made over a period of 0.5 hour.) It was found at this time that the aqueous layer had a pH of 9, presumably due to the NaOH consumption by chloroform hydrolysis. Gas chromatographic analysis of the organic layer showed that the chloroform had not completely reacted, so an additional 25 ml of 50% sodium hydroxide solution was poured into the reaction mixture. After 15 minutes at 40° C, all of the chloroform had disappeared. Analysis of the organic layer by gas liquid partition chromatography indicated that two products had been formed, as had been observed in Example 11 hereinbefore described, except now in a major/minor ratio of 85:15 rather than 93.7. An additional 25 ml of 50% sodium hydroxide solution was added, and the reaction mixture was heated to 70° C for 2 hours to determine if a base-catalyzed isomerization was taking place. However, gas liquid partition chromatography analysis of the organic layer after this time showed no change to have occurred. The organic layer was washed with water and distilled to give 40.9 grams of olefin-dichlorocarbene adduct. The trap material was not analyzed.

EXAMPLE 13

50 grams (0.43 mole) of chloroform was added to a mixture of 100 grams (1.22 moles) of cyclohexene, 100 grams of 50% aqueous sodium hydroxide solution (50 grams, 1.2 moles of NaOH) and 5.0 grams of tricaprylylmethylammonium chloride at a rate such that the temperature was maintained at 35°–40° C for a period of 1 hour. After 2 hours of stirring the mixture at 40° C, an additional 25 ml of 50% sodium hydroxide solution was added resulting in the complete reaction of the chloroform. The reaction mixture was worked up and distilled as set out in Examples 11 and 12 to yield 40 grams of 2,2-dichlorobicyclo-(1,3)heptane.

EXAMPLE 14

This example demonstrates the hydrolysis of sulfonyl chlorides by the method of the present invention according to the general equation:

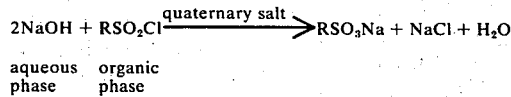

$$2NaOH + RSO_2Cl \xrightarrow{\text{quaternary salt}} RSO_3Na + NaCl + H_2O$$

aqueous    organic
phase      phase

Even with pure alkane sulfonyl chlorides, this hydrolysis as conventionally carried out is very slow unless the sulfonyl chloride is water soluble (containing, say, from 1 to 3 carbon atoms). Using the present invention, the sulfonyl chloride need not be water soluble and the reaction proceeds rapidly. Thus, a 30% solution of tridecanesulfonyl chloride in tridecane underwent hydrolysis in about 15 minutes at 25° to 50° C with a quaternary salt present. In the absence of the quaternary salt no apparent reaction took place.

EXAMPLE 15

This example demonstrates the catalytic effect of quaternary salts in the permanganate oxidation of organic compounds. A mixture of 1-octene and aqueous potassium permanganate when stirred vigorously for several hours underwent no detectable reaction. A few drops of quaternary phosphonium salt added to the mixture caused vigorous reaction to start immediately with the precipitation of manganese dioxide and the evolution of considerable heat.

EXAMPLE 16

A suspension of 10 g (0.056 mole) of stilbene in 40 ml benzene and 26.4 g (0.167 mole) of potassium permanganate partially solubilized in 50 ml of water were stirred at room temperature for 4 hours. After this time, no apparent reaction had taken place as evidenced by the absence of manganese dioxide. When two drops of tricaprylylmethylammonium chloride was added to the mixture, the reaction started immediately with the evolution of so much heat that benzene began to boil, and the mixture foamed out of the flask.

In another permanganate oxidation of the stilbene, 10 g of stilbene was added in small portions to a mixture of 40 ml of benzene, 1.0 g of tricaprylylmethylammonium chloride, 26.4 g of potassium permanganate and 50 ml of water. The rate of addition of the stilbene was controlled so that the temperature was maintained between 30° and 40° C. After the addition was completed, the reaction mixture was stirred for 0.5 hour longer. The manganese dioxide which had precipitated was separated by filtration. The filtrate was decolorized by the addition of a small amount of sodium bisulfite and was then acidified to a pH of 2 with concentrated hydrochloric acid. The benzoic acid which separated was collected on a filter and dried. It weighed 7.24 g, representing a yield of 53 percent.

EXAMPLE 17

Two reactions (A and B), identical in all respects except for the presence of a quaternary ammonium salt, were carried out. An aqueous solution, 500 ml, of paraperiodic acid (45.59 g, 0.2 mole) and osmium tetraoxide (0.10 g, 0.0004 mole) was placed in each of two three-necked flasks equipped with identical magnetic stirrers, thermometers, condensers and nitrogen inlets. A nitrogen purge, 25 ml/min, was started on each flask. To flask A was added a solution of 1-octene (22.44 g, 0.2 mole) and tetradecane (2.00 g). The mixture was stirred at room temperature. To flask B was added methyl tricaprylylammonium chloride (0.5 g) and the tetradecaneoctene solution. The mixture was stirred at room temperature but soon exothermed to 43° C. Aliquots were withdrawn periodically and analyzed by gas chromatography using the tetradecane as an internal standard. The results are listed below after correction for the individual thermal response factors. (See Table II) The results shown in the Table indicate the rate of the reaction in the presence of quaternary ammonium salt is much faster. This provides two advantages. In addition to an obvious shorter reaction time, the increase in rate should allow the quantity of osmium tetraoxide required for a rapid reaction to be reduced drastically. This would be a significant economic advantage.

TABLE II

| Time (min) | Reaction A | | | Reaction B | | |
|---|---|---|---|---|---|---|
| | 1-Octene | Heptanal | Heptanoic Acid | 1-Octene | Heptanal | Heptanoic Acid |
| 15 | 99.2 | 0.8 | 0.0 | 96.8 | 2.0 | 1.1 |
| 30 | 98.9 | 1.1 | 0.0 | 53.0 | 41.3 | 5.6 |
| 60 | 98.2 | 1.9 | 0.0 | 45.2* | 43.1 | 6.9 |
| 120 | 96.3 | 3.8 | 0.0 | | | |
| 240 | 91.0 | 9.0 | 0.0 | | | |
| 560 | 73.7 | 25.1 | 1.3 | | | |

Data in weight percent. Theoretical conversion 50%.
*This sample also contained 4.6% 1,2-octanediol. This was found to be an impurity caused by the use of excess 1-octene as the solvent. The diol was formed only after all periodate had been exhausted.

EXAMPLE 18

To a mixture of 100 g cyclohexene, 5 g of tridecylmethylammonium chloride, and 1 g of osmium tetraoxide maintained at 70° C was added 180 ml of aqueous 28 percent hydrogen peroxide solution over a period of 8 hours. A wet-test meter attached to the reaction flask showed that 360 ml of oxygen had been evolved (corresponding to 3.3 percent decomposition of the hydrogen peroxide). After cooling and standing overnight, 50 grams of sodium sulfate were dissolved in the aqueous layer to salt out organic products from the aqueous phase. The organic layer was separated and the aqueous phase was washed with ether. Analysis of the organic layer showed the yield of 1,2-cyclohexanediol to be 52 percent based on unreacted cyclohexene. The organic layer and ether washings were combined. Ether and unreacted cyclohexene were evaporated under reduced pressure and the residue distilled to give 1,2-cyclohexane diol, b.p. 60°–70° C at 0.3 mm Hg, which crystallized on standing.

EXAMPLES 19–32

In these experiments 100 g of cyclohexene, 20 g of benzene, (used as an internal gas chromatography standard for analysis), 6 g of tridecylmethylammonium chloride and 1.0 g of the metal salt were charged to the reaction flask. Aqueous hydrogen peroxide solution (27 percent) 50–100 ml was pumped through a syringe pump into the reaction mixture at 70° C over a period of 3–6 hours. Samples were periodically withdrawn from the reaction flask for analysis by gas chromatography. The amount of oxygen evolved was measured through a wet-test meter. The same procedure was repeated in several experiments, except that quaternary ammonium salt was omitted from the charge, to ascertain the effect of the quaternary ammonium salt. The results of these experiments are shown in Table III.

TABLE III

OXIDATION OF CYCLOHEXENE WITH HYDROGEN PEROXIDE[a]

| Ex. No. | Metal Compound | YIELD OF PRODUCTS (Mg e %)[b] | | | % $H_2O_2$ DECOMPOSED | |
|---|---|---|---|---|---|---|
| | | Cyclohexene Oxide | Cyclohexane and-2-ol | 1,2-cyclohexane-diol | Presence of Quaternary Salt | Absence[c] of Quaternary Salt |
| 18 | $OsO_4$ | — | — | 52.0 | 3.3 | 100 |
| 19 | $MoO_3$ | 28.4 | — | 28.3 | 2.6 | 91 |
| 20 | $H_2WO_4$ | 42.1 | — | 23.6 | 4.0 | 18 |
| 21 | $SeOCl_2$ | 4.1 | 10.2 | 46.2 | 5.0 | — |
| 22 | $V_2O_5$ | — | 88.6 | — | 5.6 | 95 |
| 23 | $Cr_2O_3$ | — | 73.5 | — | 3.0 | — |
| 24 | $TiO_2$ | 3.8 | 70.4 | — | 6.7 | — |
| 25 | $CeSO_4$ | 2.3 | 65.8 | — | 33.5 | 100 |
| 26 | NiO | 3.5 | 59.0 | — | 5.6 | — |
| 27 | $MnCl_2$ | 3.5 | 78.5 | — | 21.1 | — |
| 28 | $CoCl_2$ | 0.9 | 69.5 | — | 20.1 | — |
| 29 | $PtO_2$ | 4.9 | 74.4 | — | 44.9 | 100 |
| 30 | $FeSO_4$ | 3.8 | 65.1 | — | 26.8 | 97 |
| 31 | $Pb(OAc)_2$ | 4.3 | 76.2 | — | 5.0 | — |
| 32 | $PdCl_2$ | 17.6 | 38.6 | — | 20.5 | — |

[a]All runs contained 100 g of cyclohexene, 20 g of benzene (inert standard for gas chromatography), 5 g of tridecylmethylammonium chloride, and 1 g of metal salt. Fifty to one-hundred milliliters of 27% aqueous hydrogen peroxide was pumped into the reaction mixture, over a 3-hour period. Temperature was maintained at 70° C.
[b]Based on unreacted cyclohexane.
[c]No oxidation of cyclohexene took place in absence of quaternary salt.

EXAMPLE 33

To a mixture of 50 g of cyclohexene, 50 g of benzene, 5 g of tridecylmethylammonium chloride, 1.0 g of tungstic acid and 15 g of sodium sulfate were added 20 ml of 28 percent aqueous hydrogen peroxide over a period of 3 hours. The temperature was maintained at 40° C. Analysis of the organic layer after this time showed that 15 percent of the cyclohexene had been converted and that 1,2-epoxy cyclohexane was formed in 89 percent yield based on unreacted cyclohexene. No 1,2-cyclohexanediol was observed to have been formed.

EXAMPLE 34

1,5-Hexadiene (20 g), 2.0 g tridecylmethylammonium chloride (2.0 g), tungstic acid (0.25 g), 30 percent hydrogen peroxide in water (5 ml) and benzene (5 g, used as GLC standard) were charged to the reaction vessel. The reaction mixture was stirred at room temperature for several hours, during which time samples were periodically removed from the organic layer of the reaction and analyzed by gas chromatography. After 3 hours, approximately 15 percent of the 1,5-hexadiene had been converted to a mixture of 1,2-epoxy-5-hexene, 1,2,5,6-diepoxy hexane, 1,2-dihydroxy-5-hexene, 1,2-epoxy-5,6-dihydroxyhexane, and 1,2,5,6-tetrahydroxyhexane as major products and 1,5-hexadiene-3-one and 1,5-hexadiene-3-ol as minor products.

EXAMPLE 35

Example 34 was repeated except that 3,3-dimethyl-1-butene was substituted for 1,5-hexadiene. The principal products were 1,2-epoxy-3,3-dimethylbutane and 3,3-dimethyl-1,2-butanediol.

EXAMPLE 36

Example 34 was repeated except that a mixture of cis- and trans-2-hexene was used instead of 1,5-hexadiene. The principal products were cis- and trans-2,3-epoxyhexane and erythro- and threo-2,3-dihydroxyhexane.

EXAMPLE 37

Example 34 was repeated except that a mixture of cis- and trans-2-octene was used instead of 1,5-hexadiene. The principal products were cis- and trans-2,3-epoxy octane and erythro- and threo-2,3-dihydroxy octane.

EXAMPLE 38

Example 34 was repeated except that styrene was used instead of 1,5-hexadiene. Some styrene oxide and 2-phenyl-1,2-ethanediol were obtained, although most of the styrene polymerized.

EXAMPLE 39

Three reactions (A, B, and C) identical in all respects except for the presence of promoters and catalysts, were carried out. An aqueous solution, 500 ml, of paraperiodic acid (100.30 g, 0.44 mole) was placed in each of three 3-necked flasks equipped with magnetic stirrers, thermometers and condensers. To each flask was added solid ruthenium dioxide (0.0535 g, 0.0004 mole). The black solid immediately reacted to form a yellow solution of ruthenium tetraoxide.

To flask A was added a solution of 1-octene (11.22 g, 0.1 mole) dissolved in hexane (100 ml). The mixture was stirred at 27° C. The temperature of the reaction mixture slowly rose to 32° C and then declined.

To flask B was added a solution of 1-octene (11.22 g, 0.1 mole) and tridodecyl amine (0.5 g) dissolved in hexane (100 ml). The reaction mixture was stirred at 27° C. The reaction mixture exothermed to 35° C and then slowly cooled.

To flask C was added a solution of 1-octene (11.22 g, 0.1 mole) and Aliquot 336 (methyl tricaprylyl ammonium chloride, 0.5 g) dissolved in hexane (100 ml). The reaction mixture was stirred at 27° C. The mixture rapidly exothermed to 57° C and then slowly cooled.

Aliquots of each reaction mixture were withdrawn periodically and analyzed by gas chromatography. The thermal response factors of 1-octene and heptanal were determined from standard solutions assuming the thermal response factor for haptanoic acid was 1.0. The thermal response factors for all impurities were assumed to be 1.0. The data listed in Table IV indicate the weight percent of the three major components (1-octene, heptanel and heptanoic acid) versus time.

TABLE IV

OXIDATION OF OLEFINS

| Time, (min) | REACTION A (NO CATALYST) | | | REACTION B (TERTIARY AMINE) | | | REACTION C (QUATERNARY AMMONIUM SALT) | | |
|---|---|---|---|---|---|---|---|---|---|
| | 1-Octene | Heptanal | Heptanoic Acid | 1-Octene | Heptanal | Heptanoic Acid | 1-Octene | Heptanal | Heptanoic Acid |
| 15 | | | | | | | 13.2 | 55.6 | 30.1 |
| 30 | 91.5 | 4.9 | 1.7 | 97.9 | 1.0 | 0.0 | 0.0 | 24.9 | 74.5 |
| 45 | | | | | | | 0.0 | 6.2 | 93.2 |
| 60 | 87.2 | 8.5 | 3.5 | 90.9 | 2.9 | 4.3 | 0.0 | 0.0 | 99.3 |
| 120 | 84.3 | 6.7 | 7.9 | 75.7 | 5.0 | 15.9 | 0.0 | 0.0 | 99.4 |
| 240 | 81.0 | 8.6 | 9.3 | 46.5 | 7.6 | 39.4 | | | |
| 360 | 78.2 | 15.6 | 5.7 | 20.7 | 6.6 | 63.2 | | | |
| 480 | 78.1 | 6.1 | 14.3 | 0.0 | 2.2 | 87.4 | | | |
| 1440 | 72.6 | 12.8 | 13.6 | 0.0 | 0.0 | 93.2 | | | |

EXAMPLE 40

In the following reactions the conditions were identical in all respects except for the presence of the quaternary compound. An aqueous solution (500 ml) containing periodic acid (100.30 g, 0.44 mole) was placed in a reaction flask equipped with magnetic stirrer, thermometer and condenser. Ruthenium dioxide (0.0535 g, 0.0004 mole) was added. The black solid reacted immediately with the periodic acid to form a pale yellow solution of ruthenium tetraoxide.

In run 40-A, a solution of 1-octene (11.22g, 0.10 mole) dissolved in hexane (100 ml) was added to the flask. No quaternary compound was added to this reaction mixture. The mixture was stirred at 27° C. The temperature of the reaction mixture slowly rose to 32° C.

In run 40-B, a solution of 1-octene (11.22 g, 0.10 mole) and tributylstearyl phosphonium bromide (0.5 g) dissolved in hexane (100 ml) was added to the flask. The mixture was stirred at 28° C, but the temperature rapidly exothermed to 58° C and then slowly cooled.

Aliquots of the organic phase of each reaction mixture were withdrawn periodically and analyzed by gas chromatography. The composition of the reaction mixture was determined by comparison with a standard solution. The data listed in Table V indicate the weight percent of the three major components (1-octene, heptanal and heptanoic acid) versus time.

TABLE V

OXIDATION OF 1-OCTENE

| Run No. | 40-A | | | 40-B | | |
|---|---|---|---|---|---|---|
| Catalyst | None | | | $R_4P^+X^-$ | | |
| Time (Hrs.) | $A^1$ | $B^2$ | $C^3$ | A | B | C |
| 0.25 | | | | 46.3 | 42.3 | 11.0 |
| 0.50 | 91.5 | 4.9 | 1.7 | 16.4 | 65.7 | 17.9 |
| 0.75 | | | | 0.0 | 59.6 | 35.4 |
| 1.0 | 87.2 | 8.5 | 3.5 | 0.0 | 28.5 | 66.9 |
| 2.0 | 84.3 | 6.7 | 7.9 | 0.0 | 0.0 | 94.0 |
| 4.0 | 81.0 | 8.6 | 9.3 | | | |
| 6.0 | 78.2 | 15.6 | 5.7 | | | |
| 8.0 | 78.1 | 6.1 | 14.3 | | | |

TABLE V-continued

| | OXIDATION OF 1-OCTENE | | | | | |
|---|---|---|---|---|---|---|
| Run No. | 40-A | | | 40-B | | |
| Catalyst | None | | | $R_4P^+X^-$ | | |
| Time (Hrs.) | $A^1$ | $B^2$ | $C^3$ | A | B | C |
| 24.0 | 72.6 | 12.8 | 13.6 | | | |

$^1$A represents 1-octene.
$^2$B represents Heptanal.
$^3$C represents Heptanoic acid.

EXAMPLE 41

Sodium borohydride stock solution was prepared by dissolving 10 g (0.26 mole) of sodium borohydride in a solution of 22.6 g (0.57 mole) of sodium hydroxide in 75 ml of water. A ketone stock solution was prepared by mixing 20 ml of 2-octanone and 80 ml of benzene. These stock solutions were used to prepare reaction mixtures as follows:

| Control Run | Catalyzed Run |
|---|---|
| 50 ml ketone solution | 50 ml ketone solution |
| 30 ml borohydride solution | 30 ml borohydride solution |
| | 2.0 g tricaprylylmethyl-ammonium chloride |

Both the control run and catalyzed run were started at the same time and were stirred at the same speed. The organic layer of each run was periodically sampled and analyzed by gas chromatography as shown in Table VI.

TABLE VI

| | ANALYSIS | | | |
|---|---|---|---|---|
| | CONTROL RUN | | CATALYZED RUN | |
| Stirring Time | % 2-Octanone | % 2-Octanol | % 2-Octanone | % 2-Octanol |
| None | 22.7 | 0.00 | 22.7 | 0.00 |
| 4 Hrs at Room Temp. | 22.4 | 0.03 | 19.2 | 3.5 |
| 6.5 Hrs at Room Temp. | 22.3 | 0.04 | 19.4 | 3.3 |
| Overnight at Room Temp. | 22.2 | 0.05 | 15.1 | 7.6 |
| One Hour at 45° C | 22.1 | 0.06 | 13.1 | 9.6 |

A comparison of the data in Table II shows that the catalyzed run was 20–30 times faster than the control run, assuming first-order kinetics, or about 100 times faster assuming zero-order kinetics.

EXAMPLE 42

The quaternary salt-catalyzed alkylation of malononitrile may be represented as follows:

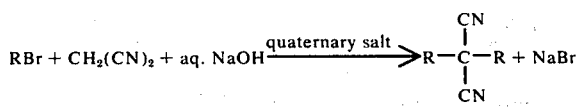

Malononitrile (128 g, 1.94 moles) was added dropwise to a mixture of 500 g (3.65 moles) of 1-bromobutane, 10 g of tricaprylylmethylammonium chloride, 146 g (3.63 moles) of sodium hydroxide and 450 ml of water. The addition rate was controlled such that the temperature was maintained at 45°–50° C. After the addition was complete, the mixture was stirred for two hours longer at 50° C. The organic layer was separated and washed twice with 300 ml portions of saturated aqueous sodium chloride. The product was then distilled to give 197 g of recovered 1-bromobutane and 170 g of 5,5-dicyanononane (87% selectivity based on 1-bromobutane) having a boiling point of 145° C at 30 mm Hg.

EXAMPLE 43

A mixture of 100 g 1-chlorooctane, 100 g of sodium cyanide, 25 ml of water, 25 ml 1-decene and 1 g of hexadecyltributylphosphonium bromide was stirred at 105° C. Samples of the organic layer were periodically removed and analyzed for 1-chlorooctane and 1-cyanooctane. A plot of this data showed that the conversion of 1-chlorooctance to 1-cyanooctane followed first order kinetics with a rate constant equal to 0.0088 minutes$^{-1}$. Additional runs were made identically except for the amount of quaternary catalyst used. The data for these runs are listed in Table VII.

TABLE VII

| Quaternary Salt Used, Grams | First Order Rate Constant, Minutes$^{-1}$ |
|---|---|
| 0.0 | No detectable Reaction |
| 1.0 | 0.0088 |
| 2.0 | 0.0172 |
| 3.0 | 0.0243 |
| 5.0 | 0.0407 |

Although certain preferred embodiments of the invention have been herein described in order to provide information and examples sufficient to enable those skilled in the art to practice the invention, many changes and innovations can be effected in the described steps, reactants utilized and reaction conditions imposed without departure from the basic principles which underlie the invention. Modification or variations of this type are deemed to be encompassed by the spirit and scope of the invention except as the same may be necessarily limited by the appended claims or reasonable equivalents thereof.

What is claimed is:

1. A process for conducting heterogeneous ionic reactions in a two-phase reaction system containing an organic phase and an aqueous phase, said reaction being conducted in the presence of an organic quaternary salt phase transfer catalyst, said salt transferring a functional reactant ion or group from either phase to the other phase, said quaternary salt being defined by $(R_1, R_2, R_3, R_4, M)^+ X^-$ wherein M is nitrogen, arsenic, phosphorus, antimony, and bismuth; X is a halide or hydroxy ion; and $R_1$, $R_2$, $R_3$, and $R_4$ are monovalent hydrocarbon radicals having a total sum of 18 to 70 carbon atoms, one of which may be further substituted by a quaternary group so that the salt is represented by

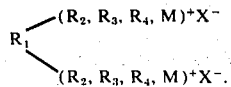

2. A process as described in claim 1 wherein M is selected from the group consisting of nitrogen, arsenic and phosphorus.

3. A process as described in claim 2 wherein M is nitrogen.

4. A process as described in claim 3 wherein X is halide.

5. A process as described in claim 3 wherein X is chlorine or bromine.

6. A process as described in claim 2 wherein M is phosphorus.

7. A process as described in claim 6 wherein X is halide.

8. A process as described in claim 6 wherein X is chlorine or bromine.

9. A process as described in claim 2 wherein the quaternary salt is selected from the group consisting of hexadecyltrihexylammonium bromide; trioctylethylammonium bromide; tridecylmethylammonium chloride, didodecyldimethylammonium chloride; tetraheptylammonium iodide; dioctadecyldimethyl ammonium chloride; tridecylbenzylammonium chloride; ditricosylmethylammonium chloride; tributyldecylphosphonium iodide; triphenyldecylphosphonium iodide; tributylhexadecylphosphonium iodide; tricapryll-dodecylammonium p-toluene sulfonate; tribenzyldecylarsonium chloride; tetranonylammonium hydroxide; tritridecylphenylstibonium chloride; triahentriacontylmethylbismuth chloride; N,N,N',N'-tetramethylN,N'-ditetradecyl-p-xylene-α,α'-di-ammonium dichloride; 1-methyl-1-(N-octadecanoyl-2-aminoethyl)-2-heptadecyl-4,5-dihydro-1,3-diazole methylsulfate; N,N,N',N'-tetramethyl-N,N'-dioctadecyl-x-dodecyl-y-xylene-α,α'-diammonium dichloride; N,N-dioctadecyl-Nmethyl-N-(sodiocarboxylmethyl)-ammonium chloride; N,N,N',N'-tetramethyl-N,N'-dioctadecyl-p-xylene-α,α'-diammonium dichloride; N,N,N',N'-tetramethyl-N,N' -dioctadecyl-1,2-ethyl-diammonium dibromide; N,N'-dimethyl-N,N,N',N'-tetraheptadecyl-2-butene-1,4-diammonium chloride.

10. A process as described in claim 2 wherein the two-phase reaction is a displacement reaction.

11. A process as described in claim 10 wherein the organic phase contains 1-chlorodecane, the aqueous phase contains a cyanide compound selected from the group consisting of potassium cyanide and sodium cyanide or mixtures of these, and the quaternary salt is dodecylbenzyltrimethylammonium chloride.

12. A process as described in claim 10 wherein the organic phase contains 1-bromodecane, the aqueous phase contains sodium acetate trihydrate, and the quaternary salt is tricaprylylmethylammonium chloride.

13. A process as described in claim 2 used for the oxidation of organic compounds with inorganic oxidizing agents.

14. A process as described in claim 13 wherein the organic compound is an olefin having one or more olefinic unsaturations selected from the group consisting of aliphatic olefins, cyclo-aliphatic olefins, or aryl olefins containing from 2 to 50 carbon atoms.

15. A process as described in claim 14 wherein the olefins are selected from the group consisting of ethylene; pentene-2; octadiene-1,5; dodecene-4; pentacosene-6; nonacosene-3; hexatriacontene-1; pentacontene-15; 3-methylhexene-1; 4-ethyloctene-2; 2-ethyl-5-butyl-23-hexyl-33-propylpentatriacontene-3; cyclobutene; cyclohexene; cyclododecene; cyclotriacontene; 1-ethyl-4-propyl-cyclooctene; 1-ethyl-3butyl 5-pentylcyclododecene; styrene; 3-methyl-styrene; stilbene; tetraphenylethylene; vinylnaphthalene; vinylanthracene; 4-butyl-1-vinylnaphthalene; 2,7-diphenyldodecene-3; 1-hexene; 1-octene; 1-decene; 1-dodecene; 1-tetradecene; internal isomers of decene; dodecene; tetradecene; hexadecene; octadecene; eicosene; vinylcyclohexene; 1,3-butadiene or alkyl substituted butadiene; vinyl chloride; vinyl acetate; oleic acid; and linoleic acid.

16. A process as described in claim 2 wherein carbonyl compounds are converted to alcohols.

17. A process as described in claim 2 used for the saponification of esters.

18. A process as described in claim 17 wherein the ester is n-hexadecyl adipate, the base is sodium hydroxide, and the quaternary salt is tricaprylylmethylammonium chloride.

19. A process as described in claim 2 used for the oxidation of olefins with inorganic oxidizing agents.

20. A process as described in claim 19 wherein in addition a metal compound selected from the group consisting of $OsO_4$, $MoO_3$, $H_2WO_4$, $SeOCl_2$, $U_2O_5$, $Cr_2O_3$, $T_iO_2$, $CeSO_4$, $NiO$, $MnCl_2$, $CoCl_2$, $PtO_2$, $FeSO_4$, $Pb(OAc)_2$, and $PdCl_2$ is present.

21. A process as described in claim 2 used for the hydrolysis of sulfonyl chlorides.

22. A process for conducting a heterogeneous ionic reaction in a two phase reaction system containing chloroform and an olefin in an organic phase and an alkaline metal base in an aqueous phase, said reaction being conducted in the presence of an organic quaternary salt phase transfer catalyst according to the general equation

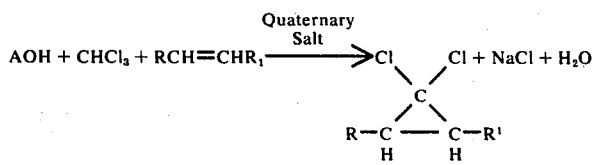

wherein said salt transfers sodium ions from the aqueous phase to the organic phase and chlorine ions from the organic phase to the aqueous phase, and wherein R and $R_1$ are independently, hydrogen or alkyl radicals containing from 1 to 5 carbon atoms and A is an alkali metal, said quaternary salt being defined by $(R_1, R_2, R_3, R_4, M)^+X^-$ wherein M is nitrogen, arsenic, phosphorus, antimony or bismuth;

X is a halide or hydroxy ion; and $R_1$, $R_2$, $R_3$ and $R_4$ are monovalent hydrocarbon radicals having a total sum of 18 to 70 carbon atoms, one of which may be further substituted by a quaternary group so that the salt is represented by

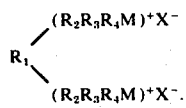

23. A process as described in claim 22 wherein the base is sodium hydroxide and the olefin is selected from the group consisting of 1-octene, 1-hexene, and cyclohexene.

24. A process as described in claim 22 wherein the quaternary salt is tricapryrylmethyl ammonium chloride.

* * * * *

UNITED STATES PATENT OFFICE
CERTIFICATE OF CORRECTION

PATENT NO. : 3,992,432
DATED : November 16, 1976
INVENTOR(S) : Donald R. Napier and Charles M. Starks It is certified that error appears in the above-identified patent and that said Letters Patent are hereby corrected as shown below:

Column 11, line 58 - delete "NaCd" and insert --NaOH---

Column 16, line 49 - delete "cyclohexehe" and insert ---cyclohexene---

Column 20, line 19 - delete "1-chlorooctance" and insert ---1-chlorooctane---

Signed and Sealed this

Twenty-ninth Day of March 1977

[SEAL]

Attest:

RUTH C. MASON
Attesting Officer

C. MARSHALL DANN
Commissioner of Patents and Trademarks